US00PP24318P2

(12) United States Plant Patent
Stemkens

(10) Patent No.: US PP24,318 P2
(45) Date of Patent: Mar. 18, 2014

(54) ***SAXIFRAGA* PLANT NAMED 'SAXZ0009'**

(50) Latin Name: *Saxifraga×arendsii*
Varietal Denomination: SAXZ0009

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 149 days.

(21) Appl. No.: 13/507,215

(22) Filed: Jun. 13, 2012

(51) Int. Cl.
*A01H 5/00* (2006.01)

(52) U.S. Cl.
USPC ..... Plt./263.1; Plt./226

(58) Field of Classification Search
USPC ..... Plt./263.1
See application file for complete search history.

(56) References Cited

U.S. PATENT DOCUMENTS

PP24,005 P2 * 10/2013 Stemkens ..... Plt./263.1
PP24,017 P2 * 11/2013 Stemkens ..... Plt./263.1

OTHER PUBLICATIONS

UPOV PLUTO 2013/04 Citations for SAXZ0009 Jun. 2012.*

* cited by examiner

*Primary Examiner* — Wendy C Haas
(74) *Attorney, Agent, or Firm* — Joshua L. Price

(57) ABSTRACT

A new *Saxifraga* plant named 'SAXZ0009' particularly distinguished by the large red-purple flowers on short peduncles held straight just above the plant with a long flowering season and good plant vigor.

1 Drawing Sheet

Latin name of the genus and species of the plant claimed: *Saxifraga×arendsii*.

Varietal denomination: 'SAXZ0009'.

BACKGROUND OF THE NEW PLANT

The present invention comprises a new *Saxifraga*, botanically known as *Saxifraga×arendsii*, and hereinafter referred to by the variety name 'SAXZ0009'.

'SAXZ0009' is a product of a planned breeding program. The new cultivar 'SAXZ0009' has large red-purple flowers on short peduncles held straight just above the plant with a long flowering season and good plant vigor.

'SAXZ0009' originates from a hybridization made in a greenhouse in April 2007 in Enkhuizen, The Netherlands. The female parent was an unpatented, proprietary plant identified as 'J1460-1' 'J1460-1' has white flower color, larger flower size and is earlier to flower than 'SAXZ0009.

The male parent of 'SAXZ0009' was an unpatented, proprietary plant identified as 'H1048-52'. 'H1048-52' has red flower color, smaller flower size and is later to flower compared to 'SAXZ0009'. The resultant seed was sown in August 2007 in Enkhuizen, The Netherlands.

'SAXZ0009' was selected as one flowering plant within the progeny of the stated cross in March 2008 in a greenhouse in Enkhuizen, The Netherlands.

The first act of asexual reproduction of 'SAXZ0009' was accomplished when vegetative cuttings were propagated from the initial selection in the March 2008 in a greenhouse in Enkhuizen, The Netherlands.

BRIEF SUMMARY OF INVENTION

Horticultural examination of plants grown from cuttings of the plant initiated March 2008 in Enkhuizen, The Netherlands, and continuing thereafter, has demonstrated that the combination of characteristics as herein disclosed for 'SAXZ0009' are firmly fixed and are retained through successive generations of asexual reproduction.

'SAXZ0009' has not been observed under all possible environmental conditions. The phenotype may vary significantly with variations in environment such as temperature, light intensity and day length.

A Plant Breeder's Right for this cultivar was applied for in Canada on Jun. 7, 2012. 'SAXZ0009' has not been made publicly available more than one year prior to the filing of this application.

The following traits have been repeatedly observed and are determined to be basic characteristics of the new variety. The combination of these characteristics distinguishes this *Saxifraga* as a new and distinct variety.

BRIEF DESCRIPTION OF THE PHOTOGRAPHS

The accompanying photographic drawings show typical flower and foliage characteristics of 'SAXZ0009' with colors being as true as possible with an illustration of this type.

Figure 1:
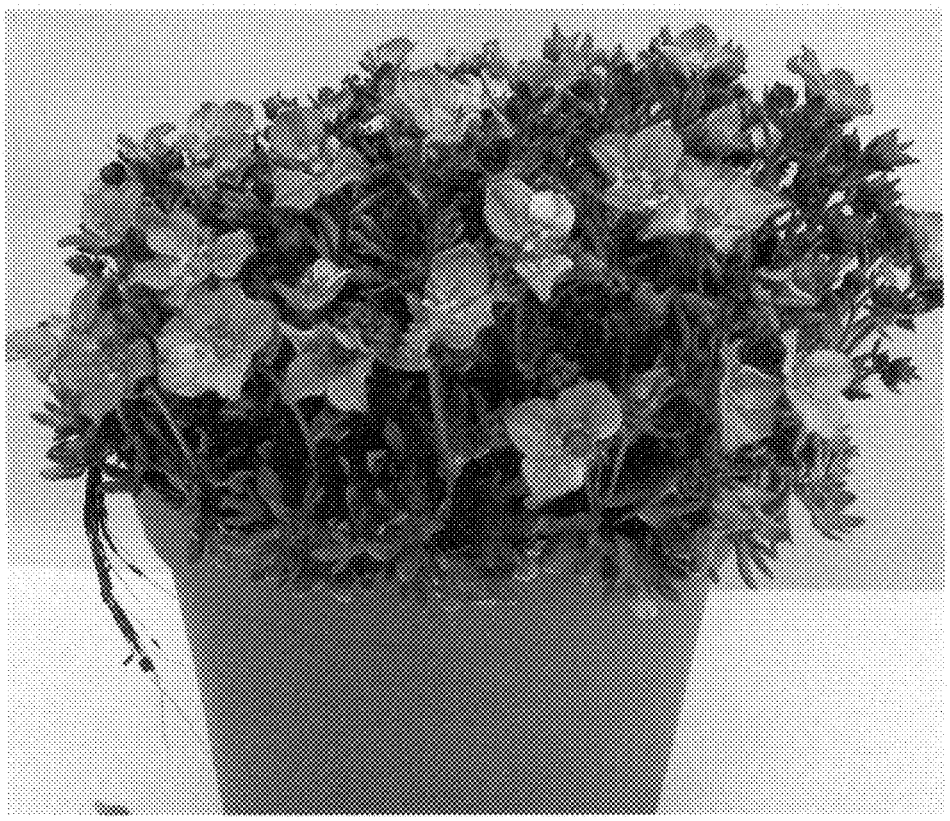
Figure 2:
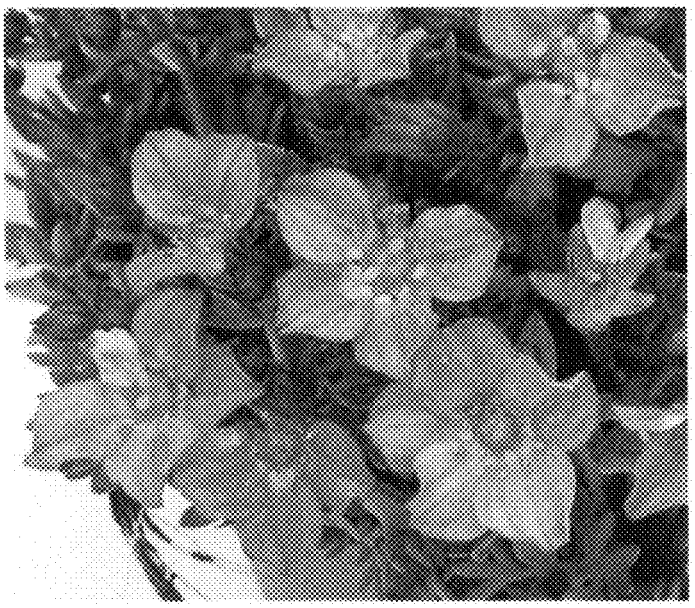

The photographic drawings show in FIG. 1 a flowering plant of the new variety and in FIG. 2 a close-up of the flowers.

DETAILED BOTANICAL DESCRIPTION

The plant descriptions and measurements were taken in Gilroy, Calif. under natural light in March 2012. These plants were approximately 24 weeks old and were growing in 1 gallon pots in shade-house trials. The plants used for the photographs were about 28 weeks old growing in Enkhuizen, The Netherlands and the photographs were taken in March 2012.

Color Chart used: Royal Horticultural Society Colour Chart (R.H.S.) 2001

TABLE 1

DIFFERENCES BETWEEN THE NEW VARIETY 'SAXZ0009' AND A SIMILAR VARIETY

| | 'SAXZ0009' | 'Rockrose' (U.S. Plant Pat. No. 19,301) |
|---|---|---|
| Initial flower color: | Lighter | Darker |
| Flower color fading habit: | Fades less | Fades more |
| Plant habit: | Less compact | More compact |

Plant:

*Form, growth and habit.*—A rosetting habit that is compact and mounded. Each rosette develops several short branched peduncles that are freely flowering.

*Plant height.*—6.0-7.0 cm.

*Plant height (inflorescence included).*—19.0-21.0 cm.

*Plant width.*—18.0-19.0 cm.

Roots:

*Number of days to initiate roots.*—About 7 days at about 18 degrees C.

*Number of days to produce a rooted cutting.*—3 weeks at 18 degrees C.

*Type.*—Fine, fibrous, free branching.

*Color.*—RHS N155B but whiter.

Foliage:

*Arrangement.*—Alternate.

*Immature, leaf color, upper surface.*—RHS 137C.

*Lower surface.*—RHS 138B.

*Mature, leaf color, upper surface.*—RHS 137C.

*Lower surface.*—RHS 138B.

*Length.*—0.5-0.7 cm.

*Width.*—0.9-1.2 cm.

*Shape.*—Spathulate; cleft-lobed.

*Base shape.*—Cuneate.

*Apex shape.*—Acute.

*Margin.*—Entire.

*Texture, upper surface.*—Glandular hairs.

*Lower surface.*—Glandular hairs.

*Color of veins, upper surface.*—Indistinct.

*Color of veins, lower surface.*—Indistinct.

*Petiole color.*—RHS 138B.

*Length.*—0.6-0.8 cm.

*Diameter.*—0.2-0.25 cm.

*Texture.*—Glandular hairs on both sides.

Lateral branching:

*Color.*—RHS 138B.

*Length of branch.*—0.2 cm.

*Diameter of branch.*—0.15 cm.

*Length of internodes.*—0.2-0.3 cm.

*Texture.*—Glandular hairs.

*Color of peduncle.*—RHS 144A.

*Length of peduncle.*—7.0-10.0 cm.

*Peduncle diameter.*—0.1 cm.

*Texture.*—Glandular hairs.

*Pedicel color.*—RHS 144A.

*Pedicel length.*—2.5-5.0 cm.

*Pedicel diameter.*—0.075 cm.

*Pedicel texture.*—Glandular hairs.

Inflorescence:

*Type.*—Simple cyme or raceme; single flower composed of 5 imbricate petals; flowers held straight above the plant and fairly flat.

*Quantity of inflorescences per plant.*—125-150 with numerous buds.

*Lastingness of individual blooms on the plant.*—About 12 days.

*Fragrance.*—None.

Bud (just before opening/showing color):

*Color.*—RHS 60B.

*Length.*—0.5-0.6 cm.

*Width.*—0.3 cm.

*Shape.*—Conical.

Corolla:

*Immature inflorescence: Diameter:* 1.5-1.7 cm. Color of petals, upper surface: Mottled hues of RHS 61B with RHS 61A veining. Lower surface: Between RHS 64C and RHS 64D with RHS 64B veining.

*Mature inflorescence: Flower diameter:* 2.4-2.6 cm. Depth: 0.7-0.8 cm. Petal color, upper surface: RHS 75B overlaid with shades of 71B to RHS 71C more heavily at the margins and veins. Lower surface: Slightly lighter than RHS 75B overlaid with shades of 71B to RHS 71C more heavily at the margins and veins. Length of petal: 0.9-1.0 cm. Width of petal: 0.7-0.8 cm. Shape: Orbicular. Apex shape: Obtuse. Margin: Entire but somewhat wavy. Petal texture, upper surface: Papillose. Lower surface: Papillose.

Calyx:

*Quantity.*—4.

*Color, upper surface.*—RHS 138B.

*Lower surface.*—RHS 138B with slight anthocyanins at the apex of about RHS 187B.

*Length.*—0.3-0.4 cm.

*Width.*—0.2 cm.

*Shape.*—Oblong.

*Apex shape.*—Acute.

*Base.*—Fused.

*Margins.*—Entire.

*Texture, upper/inner surface.*—Smooth.

*Lower/outer surface.*—Glandular hairs.

Reproductive organs:

*Gynoecium.*—

*Pistil quantity.*—1.

*Length.*—0.2 cm.

*Style color.*—RHS N144C.

*Style length.*—0.25 cm.

*Stigma color.*—RHS 154C.

*Stigma shape.*—Bi-parted.

*Ovary color.*—RHS144B.

*Ovary height.*—0.4 cm.

*Ovary width.*—0.3 cm.

*Androecium.*—

*Stamens, quantity.*—10.

*Color of filaments.*—RHS 8D.

*Length filaments.*—0.4 cm.

*Anther color.*—RHS 20B with an overlay of RHS 31B.

*Anther length.*—0.05 cm.

*Anther shape.*—Oval.

*Color of pollen.*—RHS 6B.

*Pollen amount.*—Normal.

*Fertility/seed set.*—Has not been determined to date.

*Disease/pest resistance.*—Has not been determined to date.

What is claimed is:

1. A new and distinct variety of *Saxifraga* plant named 'SAXZ0009' substantially as illustrated and described herein.

* * * * *